United States Patent
Hoshino

(10) Patent No.: US 9,572,541 B2
(45) Date of Patent: Feb. 21, 2017

(54) EQUIVALENT PHANTOM AND METHOD OF EVALUATING QUALITY OF X-RAY TALBOT IMAGING APPARATUS WITH THE SAME

(71) Applicant: Konica Minolta, Inc., Chiyoda-ku, Tokyo (JP)

(72) Inventor: Yoshihide Hoshino, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 86 days.

(21) Appl. No.: 14/710,996

(22) Filed: May 13, 2015

(65) Prior Publication Data

US 2015/0327834 A1 Nov. 19, 2015

(30) Foreign Application Priority Data

May 13, 2014 (JP) ................................ 2014-099195

(51) Int. Cl.
*A61B 6/00* (2006.01)
*G21K 1/06* (2006.01)

(52) U.S. Cl.
CPC ............... *A61B 6/484* (2013.01); *A61B 6/505* (2013.01); *A61B 6/5217* (2013.01); *G21K 1/067* (2013.01); *A61B 6/583* (2013.01)

(58) Field of Classification Search
CPC ....... A61B 6/484; A61B 6/5217; A61B 6/505; A61B 6/583; G21K 1/067
USPC ...................................... 378/70, 86, 87, 207
See application file for complete search history.

(56) References Cited

U.S. PATENT DOCUMENTS

2011/0243305 A1* 10/2011 Tada ................... A61B 6/4291
378/87

FOREIGN PATENT DOCUMENTS

| JP | 2008200359 A | 9/2008 |
|---|---|---|
| WO | 2008102685 A1 | 8/2008 |
| WO | 2011033798 A1 | 3/2011 |

OTHER PUBLICATIONS

A. Momose et al., "Phase Tomography by X-ray Talbot Interferometry for Biological Imaging," Japanese Journal of Applied Physics; Jun. 2006, pp. 5254-5262, vol. 45, No. 6A.
K. Hibino et al., "Phase Shifting for Nonsinusoidal Waveforms with Phase-shift Errors," The Journal of the Optical Society of America; Apr. 1995, pp. 761-768, vol. 12, No. 4.
M. Takeda et al., "Fourier-transform Method of Fringe-pattern Analysis for Computer-based Topography and Interferometry," Journal of the Optical Society of America; Jan. 1982, pp. 156-160, vol. 72, No. 1.

* cited by examiner

*Primary Examiner* — Michael Maskell
(74) *Attorney, Agent, or Firm* — Cantor Colburn LLP

(57) ABSTRACT

An equivalent phantom is used for an X-ray Talbot imaging apparatus which includes an X-ray source, a plurality of gratings and an X-ray detector. The apparatus captures at least a Moire image from which a differential phase image of an object is generated. The equivalent phantom includes a first substance having a first refractive index and a second substance having a second refractive index. A ratio of the first refractive index to the second refractive index is equal to a ratio of a refractive index of a soft tissue to a refractive index of a surrounding tissue. At least a part of a shape of one of the first and second substances is equal to a shape of a corresponding portion of the soft tissue.

9 Claims, 8 Drawing Sheets

FIG. 7

| EQUIVALENT PHANTOM | CURVATURE RADIUS | SPECIFIC GRAVITY | SIGNAL LEVEL Imax-Iave | NOISE ΔI | S/N RATIO | IRRADIATION CONDITION |
|---|---|---|---|---|---|---|
| CYLINDRICAL MEMBER | ○○mm | ○○g/cm3 | ○○○LSB | ○○○LSB | ○○ | TUBE VOLTAGE ○○kV<br>TUBE CURRENT ○○mA<br>IRRADIATION TIME ○○ms |

EQUIVALENT PHANTOM AND METHOD OF EVALUATING QUALITY OF X-RAY TALBOT IMAGING APPARATUS WITH THE SAME

CROSS REFERENCE TO RELATED APPLICATIONS

The present invention claims priority under 35 U.S.C. §119 to Japanese Application No. 2014-099195 filed May 13, 2014, the entire content of which is incorporated herein by reference.

BACKGROUND OF THE INVENTION

Field of the Invention

The present invention relates to an equivalent phantom and a method of evaluating the quality of the X-ray Talbot imaging apparatuses with the equivalent phantom.

Description of Related Art

An X-ray imaging apparatus is known, which is provided with a Talbot interferometer or a Talbot-Lau interferometer and an X-ray detector (Flat Panel Detector: FPD) and captures and visualizes phase shift of X-rays passing through an object (see, for example, Japanese Unexamined Patent Application Publication No. 2008-200359; WO2011/033798; K. Hibino et al, J. Opt. Soc. Am. A, Vol. 12, (1995) p. 761-768; A. Momose et al, J. Appl. Phys., Vol. 45, (2006) p. 5254-5262; and M. Takeda et al, J. Opt. Soc. Am, Vol. 72, No. 1, (1982) p. 156). The X-ray imaging apparatus provided with such a Talbot or Talbot-Lau interferometer is hereinafter referred to as X-ray Talbot imaging apparatus.

The X-ray Talbot imaging apparatus includes a first grating (also known as a G1 grating) and a second grating (also known as a G2 grating), each consisting of slits at constant intervals, and an optional X-ray source grating, if a Talbot-Lau interferometer is included. An X-ray source emits X-rays to the first grating to produce an image of the first grating itself at a focused position downstream of the first grating in the direction of traveling X-rays. The second grating is disposed at this position in such a manner that the array of slits of the second grating is slightly slanted to the array of the slits of the first grating. This slanted disposition produces Moire fringes onto the second grating. These Moire fringes are superimposed to produce an image (Moire image, hereinafter). The image is detected and visualized by the X-ray detector disposed downstream of the second grating.

An object placed between the X-ray source and the first grating distorts the Moire fringes. The X-ray Talbot imaging apparatus moves the first and second gratings relatively to each other to capture plural Moire images (Fringe scanning mode). The Moire images are analyzed through image processing to reconstruct images such as a differential phase image, an X-ray absorption image, and a small angle scattering image. Alternatively, a Moire image of an object captured with the X-ray Talbot imaging apparatus is processed through, for example, Fourier transformation to reconstruct an image such as a differential phase image (Fourier transformation method).

Conventional images such as an X-ray absorption image (see FIG. 8A) have not been able to include a cartilage end (exactly, an "interface" between a cartilage and surrounding joint fluid in a joint, hereinafter). The present inventors have found that a differential phase image reconstructed from the Moire image as described above can include a cartilage end as shown with an arrow in FIG. 8B. The study by the inventors also shows that the differential phase image can include not only joint cartilages but also, for example, human soft tissues such as Achilles tendons and tumor masses.

Such a differential phase image reconstructed from the Moire image captured with the X-ray Talbot imaging apparatus can include a joint cartilage end, only if each grating such as the first grating is precisely manufactured (or, within an allowable manufacturing tolerance), and if the X-ray Talbot imaging apparatus is well evaluated and controlled in quality such that MTFs (Modulation Transfer Function) of a X-ray source tube and the X-ray detector are in good conditions. If the quality is not properly evaluated or controlled, the differential phase image cannot include soft tissues such as a joint cartilage.

The evaluation and control of quality as well as improvement in quality have been performed for individual components of the X-ray Talbot imaging apparatus. For example, an X-ray source tube has been evaluated through imaging of a test pattern to determine the diameter of a focal spot; an X-ray detector (FPD) through imaging of its profile and edges with X-rays to determine the MTF; or the manufacturing accuracy of the grating through comparison of Moire images at the start and the end of the operation of an X-ray Talbot imaging apparatus to check for any distortion in relative positions to adjust individual components, as described in WO 2008/102685.

Even if each component were evaluated and/or adjusted, the component of the X-ray Talbot imaging apparatus would deteriorate in quality over time. Therefore, it is not always ensured that a differential phase image reconstructed from the Moire images captured with the X-ray Talbot imaging apparatus includes soft tissues of joint cartilages. In other words, to ensure capture of soft tissues of joint cartilages in a differential phase image reconstructed from the Moire images captured with the X-ray Talbot imaging apparatus, the quality of the X-ray Talbot imaging apparatus itself, that is, the overall quality of the X-ray Talbot imaging apparatus should be evaluated.

The X-ray Talbot imaging apparatus, however, is still in the development phase and has no criteria required for evaluation. If the X-ray Talbot imaging apparatus is regarded as an imaging apparatus to draw an image of a soft tissue in a differential phase image, it is preferable in imaging an object that the quality of the X-ray Talbot imaging apparatus is defined as the image quality of the differential phase image reconstructed from the Moire image captured with the X-ray Talbot imaging apparatus.

If the image quality is defined such that the image quality of human soft tissues can be estimated by imaging the equivalent phantom with the X-ray Talbot imaging apparatus, variations in quality between apparatuses and days can be controlled. In addition, different types of imaging apparatuses also can be compared in quality, which is practically advantageous.

SUMMARY OF THE INVENTION

An object of the present invention, which has been accomplished to solve the above issues, is to provide an equivalent phantom for evaluating the quality of an X-ray Talbot imaging apparatus and a method of evaluating the quality of an X-ray Talbot imaging apparatus with the equivalent phantom.

In order to realize the above object, according to a first aspect of the present invention, there is provided an equivalent phantom for an X-ray Talbot imaging apparatus which includes an X-ray source, a plurality of gratings and an X-ray detector, and which captures at least a Moire image from which a differential phase image of an object is generated, the equivalent phantom including:
a first substance having a first refractive index; and
a second substance having a second refractive index, wherein a ratio of the first refractive index to the second refractive index is equal to a ratio of a refractive index of a soft tissue to a refractive index of a surrounding tissue, and
wherein at least a part of a shape of one of the first and second substances is equal to a shape of a corresponding portion of the soft tissue.

According to a second aspect of the present invention, there is provided a method of evaluating quality of an X-ray Talbot imaging apparatus including:
an X-ray source which emits X-rays;
a plurality of gratings; and
an X-ray detector which includes conversion elements which generate electric signals in accordance with the emitted X-rays, and which reads the electric signals generated at the conversion elements as a Moire image, the method including:
emitting X-rays from the X-ray source to the equivalent phantom to capture the Moire image;
generating, from the Moire image of the equivalent phantom, at least a differential phase image or an image based on the differential phase image; and
evaluating the quality of the X-ray Talbot imaging apparatus with the generated differential phase image or the image based on the differential phase image.

The equivalent phantom and the method of evaluating the quality of an X-ray Talbot imaging apparatus with the equivalent phantom according to the present invention can precisely create the shapes of soft tissues with a first substance of the equivalent phantom and the ratio of the refractive index of a soft tissue to the refractive index of the surrounding tissue with the first substance and a second substance of the equivalent phantom. The equivalent phantom is irradiated with X-rays to capture a Moire image, and then the Moire image is used to generate a differential phase image. The differential phase image includes one or more portions of the interfaces between the first and second substances of the equivalent phantom. From the portion (s), a profile of pixel values I (see FIG. 4 described later) can be produced in the differential phase image including an actual soft tissue and the surrounding tissue.

From this profile, the maximum value, etc. of the pixel values I is calculated. The maximum value, etc. can be used as an index to accurately evaluate the image quality of the differential phase image; hence, the equivalent phantom according to the present invention can control, maintain, and improve the quality of the X-ray Talbot imaging apparatus.

BRIEF DESCRIPTION OF THE DRAWINGS

The present invention will become more fully understood from the detailed description given hereinbelow and the appended drawings which are given by way of illustration only, and thus are not intended as a definition of the limits of the present invention, and wherein.

FIG. 7 is a table listing evaluated results such as a maximum pixel value and an S/N ratio at the interface.

DETAILED DESCRIPTION OF THE PREFERRED EMBODIMENT

Hereinafter, an embodiment of the present invention will be described with reference to the drawings. Though various technical limitations which are preferable to perform the present invention are included in the after-mentioned embodiment, the scope of the invention is not limited to the following embodiment and the illustrated examples.

Embodiments of the equivalent phantom and the method of evaluating the quality of the X-ray Talbot imaging apparatus with the equivalent phantom according to the present invention will now be described, with reference to the attached drawings.

Although the X-ray Talbot imaging apparatus includes the Talbot-Lau interferometer that includes a radiation source grating (also referred to as a multi grating or a multi slit) in addition to a first grating and a second grating, the description is also applicable to any other X-ray Talbot imaging apparatus that includes no radiation source grating.

Configuration of X-Ray Talbot Imaging Apparatus

Figure 1:
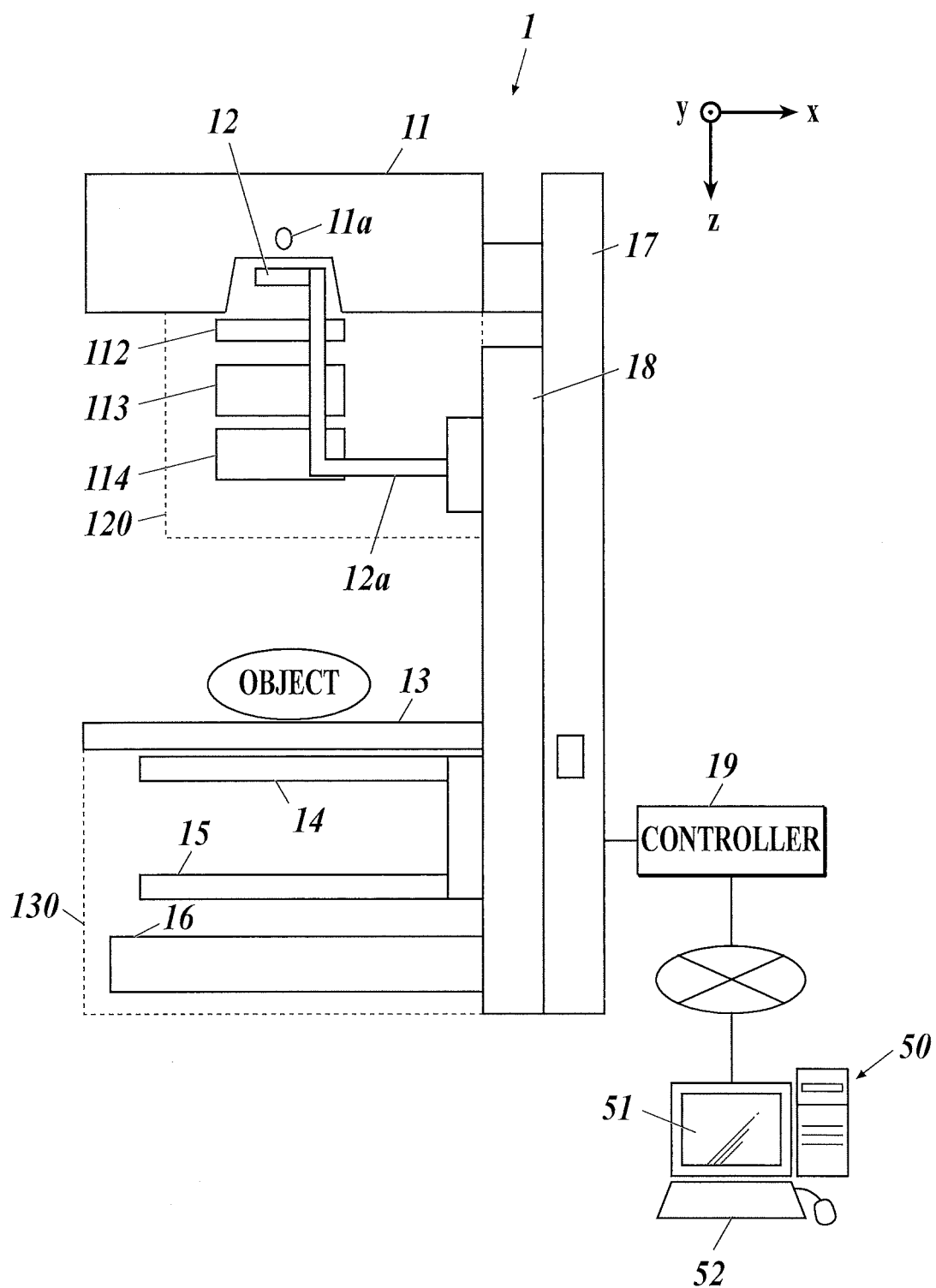
FIG. 1 is a schematic view illustrating a configuration of an X-ray Talbot imaging apparatus of one embodiment.

A configuration of the X-ray Talbot imaging apparatus of the embodiment will now be described. FIG. 1 is a schematic view illustrating the configuration of the X-ray Talbot imaging apparatus of the embodiment. In FIG. 1, the X-ray Talbot imaging apparatus 1 includes an external device 50, such as a computer connected via a network.

In the embodiment, as shown in FIG. 1, the X-ray Talbot imaging apparatus 1 includes an X-ray generator 11, an X-ray source grating 12, an object stage 13, a first grating 14, a second grating 15, an X-ray detector 16, a pillar 17, a base 18, and a controller 19. Although the X-ray generator 11 provided at an upper portion of the X-ray Talbot imaging apparatus 1 emits X-rays downwardly to an object placed below as shown in FIG. 1, X-rays may be emitted in any directions, such as a horizontal direction. The present invention can also be applied to such a case.

In the embodiment, the X-ray generator 11 includes an X-ray source 11a, which is, for example, a Coolidge X-ray source or a rotating anode X-ray source that have been widely used in the medical field. Alternatively, any other X-ray source may be used. The X-ray source grating 12 is provided below the X-ray source 11a. To prevent vibration of the X-ray generator 11 caused by, for example, the rotation of the anode of the X-ray source 11a from propagating to the X-ray source grating 12, the X-ray source grating 12 is attached not to the X-ray generator 11 but to a fixing member 12a attached to the base 18 on the pillar 17.

In the embodiment, the X-ray source grating 12, the first and second gratings 14 and 15 have multiple slits S (see FIG. 2 described later) disposed therein at predetermined intervals in the y direction perpendicular to the z direction of emitted X-rays. This indicates that the slits S and the gratings (not shown) alternating with the slits S extend in the x direction.

In the embodiment, the fixing member 12a described above includes a filter (or an additional filter) 112 for modifying the characteristics of X-rays passing through the X-ray source grating 12, an irradiation field stop 113 for narrowing the field irradiated with X-rays, and an irradiation field lamp 114 for emitting visible light instead of X-rays toward the object for positioning before the X-ray emission, if required, in addition to the X-ray source grating 12. The X-ray source grating 12, the filter 112, and the irradiation field stop 113 may be disposed in any order. In the embodiment, a first protective cover 120 is also disposed around the X-ray source grating 12, etc. for protection.

The object stage 13 is disposed between the X-ray generator 11 and the first grating 14, to hold patient's joint or other portions to be imaged. For example, when the object is a joint of patient's hand (such as a MP joint) and its cartilage, the hand is placed on the object stage 13 as shown in FIG. 2, such that the hand is perpendicular to the direction of the slits S of the first grating 14 (i.e., the direction of the grating), then the object is imaged.

Figure 2:
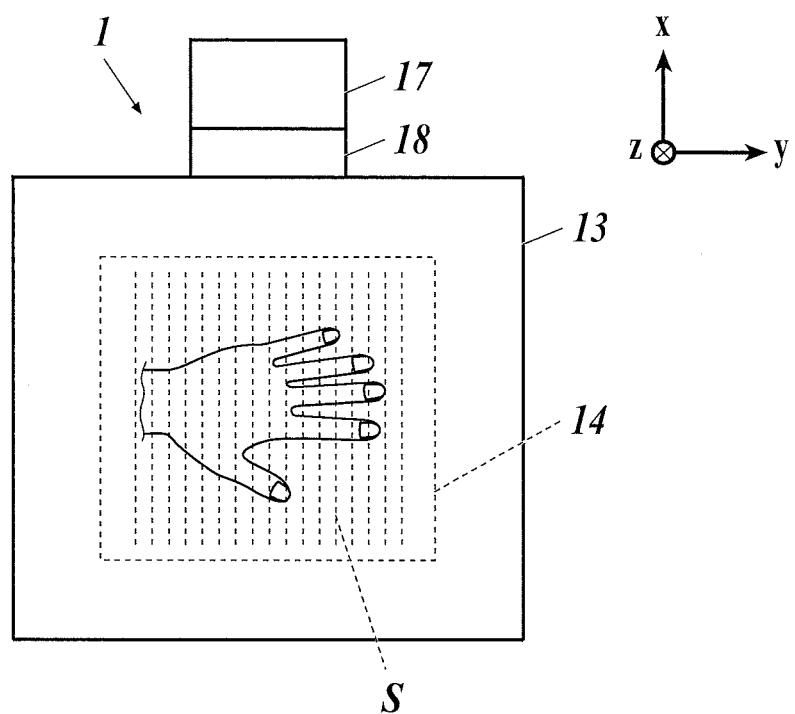
FIG. 2 illustrates a positional relation between the direction of patient's hand placed on an object stage and the direction of the slits of, for example, a first grating in imaging of joint cartilages of the hand and fingers.
Figure 8A:
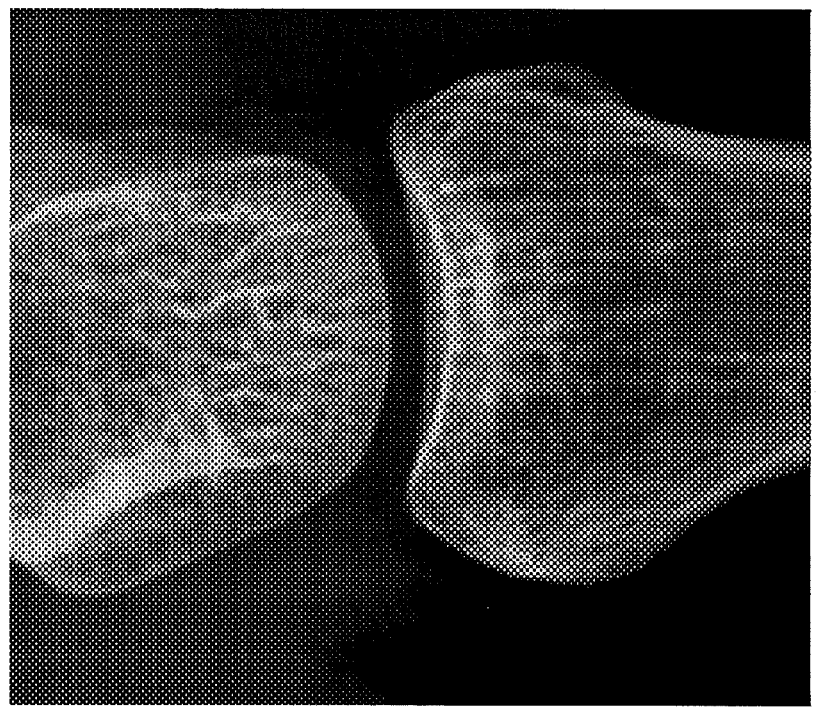
FIG. 8A is an exemplary X-ray absorption image of a joint.
Figure 8B:
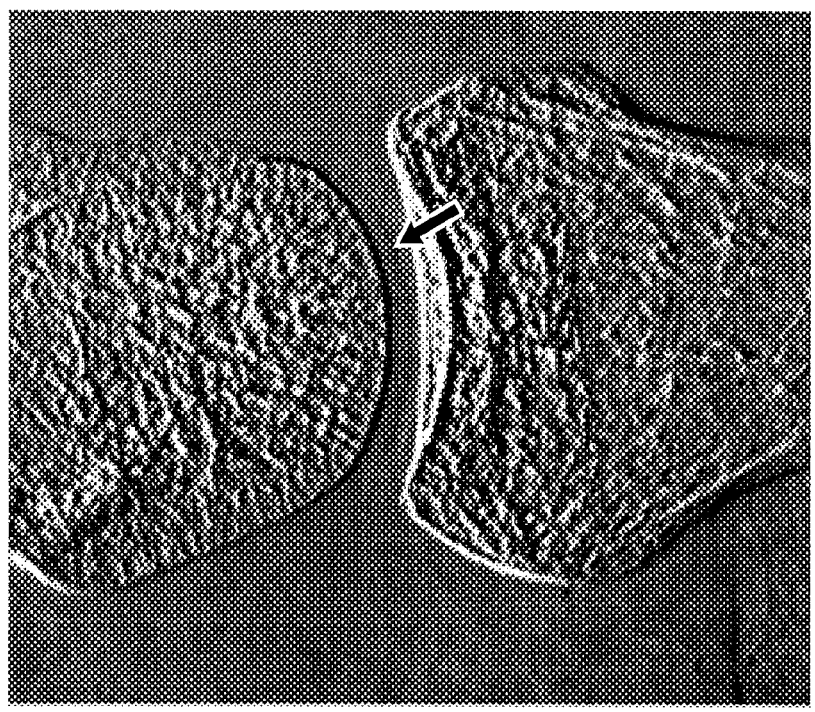
FIG. 8B is a photograph of an exemplary differential phase image of a joint and a cartilage end of the joint captured in the exemplary differential phase image.

FIG. 2 represents only the relative positional relationship among patient's hand, the object stage 13, the first grating 14, the slits S and so on, and does not represent the actual relative sizes of these components of the imaging apparatus. The hand is imaged in this way to capture a Moire image, from which an X-ray absorption image and a differential phase image are generated as shown in FIGS. 8A and 8B. The images reconstructed from the Moire image captured with the X-ray Talbot imaging apparatus 1, including the differential phase image, the X-ray absorption image, a small angle scattering image, and any other images generated from (i.e., obtained by processing) these images, are referred to as reconstructed images, hereinafter.

The first and the second gratings 14 and 15 are disposed below the object stage 13. The second grating 15 is, as described above, disposed at a position downstream of the first grating 14 in the direction of emitted X-rays (i.e., z direction), on which the image of the first grating 14 irradiated with X-rays from the X-ray source 11a is produced at constant intervals. In addition, the second grating 15 is disposed such that the direction of the slits of the second grating is slightly slanted to the direction of the slits of the first grating.

The X-ray detector 16 is disposed right below the second grating 15. Conversion elements (not shown) are disposed on the X-ray detector 16 to generate electric signals in accordance with the received X-rays. The X-ray detector 16 reads the electric signals from the conversion elements as image signals to capture the mentioned Moire image produced on the second grating 15. A second protective cover 130 is disposed around the first and second gratings 14 and 15, and the X-ray detector 16, for protecting them from collisions of patient's body such as a foot.

When the X-ray Talbot imaging apparatus 1 is operated in a fringe scanning mode to capture two or more Moire images, the X-ray Talbot imaging apparatus 1 includes a transfer device (not shown) to move any one of the X-ray source grating 12, the first and second gratings 14 and 15, or both of the first and second gratings 14 and 15 in the y direction perpendicular to the direction (x direction) of the gratings and the slits provided thereon. The present invention can also be applied in the case where the X-ray Talbot imaging apparatus 1 is not operated in a fringe scanning mode to capture only one Moire image and then analyzes the Moire image through Fourier transformation by the controller 19 and/or the external device 50 to reconstruct an image such as a differential phase image.

In the embodiment, the controller 19 includes a CPU (Central Processing Unit), ROM (Read Only Memory), RAM (Random Access Memory), and a computer connected to a bus via an input/output interface (all not shown). Alternatively, the controller 19 may be a dedicated controller. The controller 19 includes accessory devices and/or apparatuses (not shown), such as an input device and a display device.

The controller 19 controls the X-ray Talbot imaging apparatus 1. For example, the controller 19 determines the voltage of the X-ray tube and/or an emission time of the X-ray generator 11. Alternatively, when the X-ray Talbot imaging apparatus 1 is operated in a fringe scanning mode to capture two or more Moire images as described above, the controller 19 controls the distance the rate, etc. of the movement of the first grating 14, etc. via the transfer device and performs processing such as adjustment of the temporal relationship between the X-ray emission from the X-ray generator 11 and the movement of the grating.

In the embodiment, the controller 19 also functions as a generator that controls the X-ray generator 11, but it is also possible to provide a generator separately from the controller 19.

In the embodiment, the controller 19 also functions as an image processor that generates the reconstructed images such as a differential phase image (see FIG. 8B, for example), an X-ray absorption image (see FIG. 8A, for example), and a small angle scattering image from one or more Moire images captured by the X-ray detector 16. The controller 19 may be of any type that can generate the differential phase image among these reconstructed images and/or a new image from the differential phase image, and not necessarily required to generate the X-ray absorption image and the small angle scattering image.

Instead of generating the reconstructed images, such as a differential phase image, from a Moire image, the controller 19 of the X-ray Talbot imaging apparatus 1 may send data of the Moire image to the external device 50 (i.e., image processor) connected via the network, etc., and the external device 50 may generate a reconstructed image, such as a differential phase image, from the data. In FIG. 1, the reference numeral 51 is a display device of the external device 50, and the reference numeral 52 is an input device, such as a mouse and a keyboard, of the external device 50.

Configuration of Equivalent Phantom

The configuration of the equivalent phantom, which is used for defining the quality of the X-ray Talbot imaging apparatus 1, will now be described. Functions of the equivalent phantom according to the embodiment will also be described.

During the maintenance work of the X-ray Talbot imaging apparatus 1, the equivalent phantom is placed instead of a human body of interest on the object stage 13. The equivalent phantom on the object stage 13 is irradiated with X-rays by predetermined number of times (the fringe scanning mode), or once (the Fourier transform method), from the X-ray source 11a of the X-ray generator 11 to capture one or more Moire image.

The dose of X-rays emitted from the X-ray source 11a of the X-ray Talbot imaging apparatus 1 is varied with required doses for individual objects such as a joint cartilage of a hand or a knee or a soft tissue of an Achilles tendon. The equivalent phantom used for evaluation and/or control of the quality of the X-ray Talbot imaging apparatus 1 is irradiated with X-rays at the same dose as that emitted to an actual object to capture a Moire image.

In the embodiment, the equivalent phantom includes a first substance and a second substance. The ratio of a refractive index of the first substance to that of the second substance is equalized to the ratio of a refractive index of a soft tissue (e.g., a cartilage of a finger) to its surrounding tissue (e.g., joint fluid around the cartilage). In addition, one corresponding to the soft tissue of the first and second substances has at least partly the same shape as that of a corresponding portion (that can be represented by a circular arc) of the soft tissue.

Terms "same" and "be equalized" used in descriptions hereinafter (and in the claims) do not indicate that the equivalent phantom is formed such that the ratio of the refractive index of the first substance to that of the second substance is equal to that of the soft tissues of individual patients (e.g., a cartilage and its surrounding joint fluid of a phalangeal joint), and one of the first and second substances is formed to be at least partly the same in shape as that of the corresponding portion of the soft tissue of individual patients.

Although the X-ray Talbot imaging apparatus 1 can be adjusted to properly image the soft tissue if the equivalent phantom were formed for individual objective soft tissues of every patient, it is not practical to adjust the X-ray Talbot imaging apparatus 1 so as to properly image individual soft tissues of every patient. In general, the equivalent phantom is tailored to the average transmittance, shape, and/or size of soft tissues (e.g., a phalangeal joint). The equivalent phantom may be tailored to adults, infants, or sex. Alternatively, the equivalent phantom may be tailored to individual imaging objects such as a phalangeal joint or a knee joint.

Thus, the terms "same" and "be equalized" should not be understood to indicate that the equivalent phantom is formed to have the same transmittance, shape, and/or size as those of individual soft tissues of individual patients, but to indicate that the equivalent phantom is tailored to, for example, the average transmission.

Several exemplary configurations of the embodiment will now be described below.

Exemplary Configuration 1

Figure 3A:
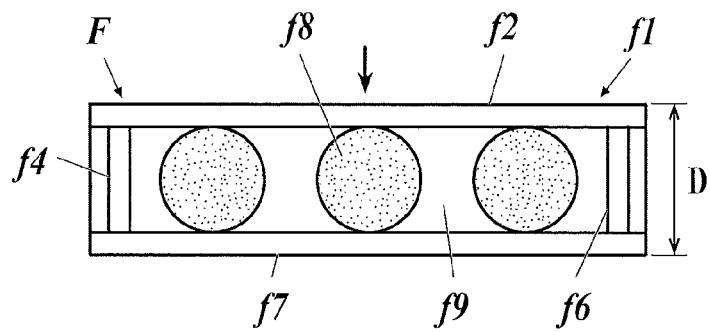
FIG. 3A is a front view illustrating an exemplary configuration of the equivalent phantom.
Figure 3B:
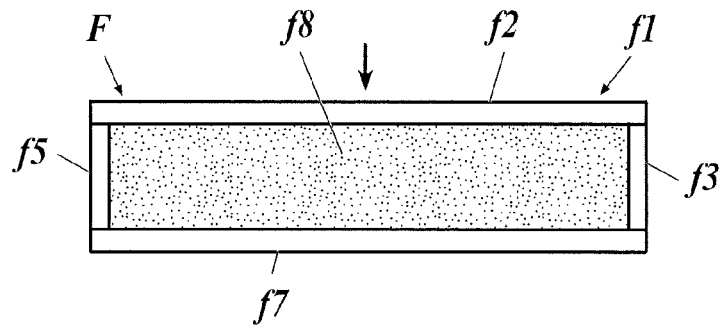
FIG. 3B is a side view illustrating an exemplary configuration of the equivalent phantom.
Figure 3C:
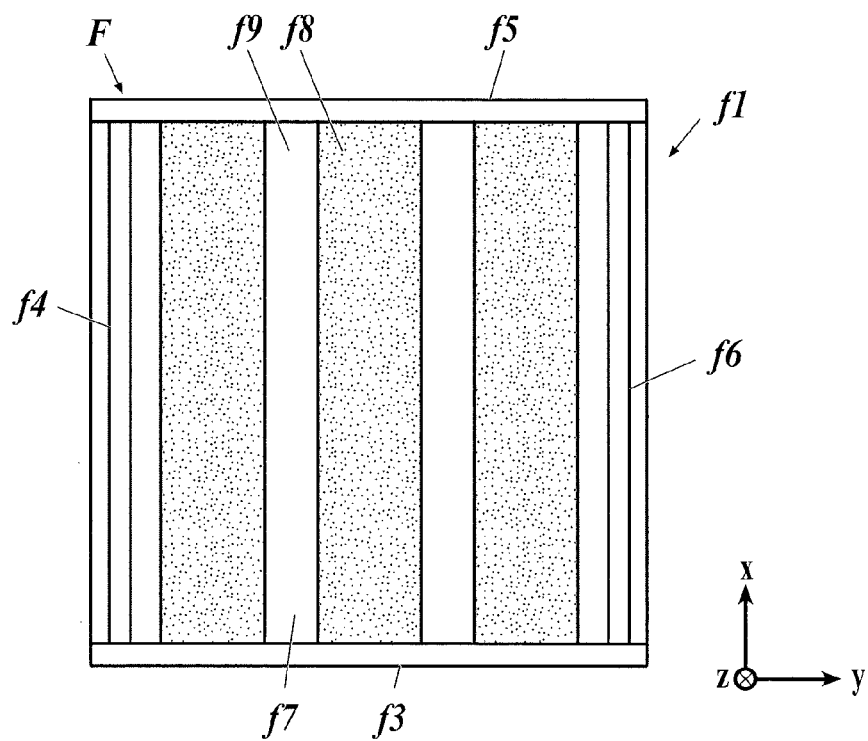
FIG. 3C is a plane view illustrating an exemplary configuration of the equivalent phantom.

FIGS. 3A to 3C are a front view, a side view, and a plan view, respectively of an exemplary configuration 1 of the equivalent phantom F. In FIGS. 3A to 3C, the most proximal plane (a side f3 in FIG. 3A, a side f4 in FIG. 3B, and a top lid f2 in FIG. 3C) is not depicted to visualize the inside of the equivalent phantom F. Arrows in FIGS. 3A and 3B indicate the direction of incident X-rays. The equivalent phantom F is placed on the object stage 13 of the X-ray Talbot imaging apparatus 1 such that a cylindrical member f8 extends in the x direction (see FIGS. 2 and 3C). Thus, the cylindrical member f8 placed on the object stage 13 extends parallel to or slightly slanted to the direction of the slits S of the grating.

In the exemplary configuration 1, the equivalent phantom F includes a housing f1 including the top lid f2, the sides f3 to f6, and a bottom f7. The housing f1 accommodates the cylindrical member f8 and fluid f9 surrounding the cylindrical member f8. The cylindrical member f8 is formed of a substance corresponding to a cartilage of a phalangeal joint, and the fluid f9 is a substance corresponding to the joint fluid surrounding the cartilage.

The top lid f2, the sides f3 to f6, and the bottom f7 of the housing f1 as well as the cylindrical members f8 are formed of an acrylic resin having high workability and high water and chemical resistances. Alternatively, they may be formed of any other material, for example, glass. The housing f1 and the cylindrical member f8 may be formed of different materials. The materials may be selected independently as required. For example, the housing f1 is formed of a plastic material and the cylindrical member f8 a glass material. Because the material does not require transparency but does require X-ray permeability, the housing f1 and the cylindrical member f8 may be translucent or opaque.

Dents having the same diameter as the cylindrical members f8 are provided at predetermined positions on the sides f3 and f5. Each cylindrical member f8 is fitted into the dent to be held by the sides f3 and f5, such that the cylindrical member f8 is fixed in the housing f1.

When the equivalent phantom F is irradiated with X-rays to capture a Moire image to generate a differential phase image (including a composite image obtained through processing of the differential phase image, hereinafter), the equivalent phantom F needs to reproduce an imaging condition that can image an interface between a soft tissue and the surrounding tissue (e.g., an interface between a cartilage and surrounding joint fluid in a joint (see an arrow shown in FIG. 8B)).

Hence, in the exemplary configuration 1, the equivalent phantom F meets the following conditions.

Condition 1

The ratio of the refractive index of the cylindrical member f8 of the first substance to the refractive index of the fluid f9 of the second substance should equal to the ratio of the refractive index of a soft tissue to the refractive index of the surrounding tissue to be imaged.

As described above, the differential phase image generated from a Moire image captured with the X-ray Talbot imaging apparatus 1 can image the interface between a cartilage of finger and knee joints, an Achilles tendon, etc., or a soft tissue of a tumor mass, etc. and the surrounding tissue for the following reason. The pixel value of each pixel in the differential phase image is proportional to the ratio of the refractive indices of individual substances at the interface corresponding to the pixel between human tissues.

The pixel values of pixels in a soft tissue (e.g., a cartilage) are substantially identical to each other because the refractive index is almost even over the soft tissue. Also, the pixel values of pixels in the surrounding tissue (e.g., joint fluid) of the soft tissue are substantially identical to each other because the refractive index is almost even over the surrounding tissue. The refractive index, however, changes at the interface between the soft tissue and the surrounding tissue; hence, the signals at the interface are depicted as shown in FIG. 8B in a differential phase image.

Figure 4:
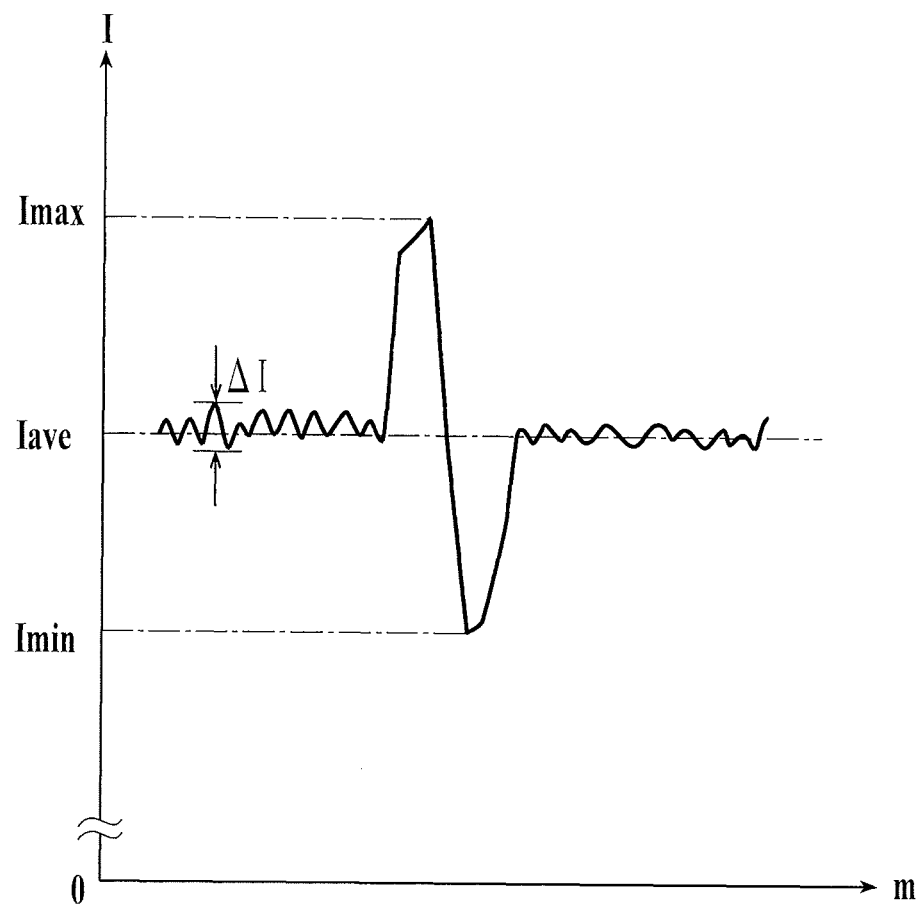
FIG. 4 is a graph showing a profile of pixel values in a differential phase image shown in FIG. 8B in view from the left to right.

When the pixel value I of a pixel at the interface between a cartilage and joint fluid in the differential phase image shown in FIG. 8B is plotted from the left to the right, the pixel value I significantly increases and then decreases at the interface as shown in the profile of the pixel values I shown in FIG. 4. The increase and decrease of the pixel values I correspond to the change in the refractive index at the interface. The vertical axis m in FIG. 4 indicates pixel numbers. Symbols Iave, Imax, Imin and ΔI in FIG. 4 will be described later.

The equivalent phantom F should be formed so as to reproduce the profile of the pixel values I as shown in FIG. 4, that is, a change in the refractive index to provide such a profile of the pixel values I.

According to the study by the inventor, the only requirement for the equivalent phantom F is condition 1 described above, that is, the ratio of the refractive index of the cylindrical member f8 of the first substance to that of the fluid f9 of the second substance should be equal to the ratio of the refractive index of a soft tissue to that of the surrounding tissue (i.e., a cartilage and a joint fluid in the example above).

Thus, the refractive indices n8 and n9 of the cylindrical member f8 and the fluid f9 are selected to meet the following expression:

$$n8/n9 = nc/nt \quad (1)$$

where, n8, n9, nt, and nc are the refractive indices of the cylindrical member f8, the fluid f9, the soft tissue, and the surrounding tissue, respectively.

When the cylindrical member f8 is composed of an acrylic resin as described above, the refractive index n8 of the cylindrical member f8 is equal to the refractive index of the acrylic resin. Although any other substance may be added to the cylindrical member f8 to modify the refractive index n8, it is not practical to prepare different cylindrical members f8 having properly adjusted refractive indices.

Preferably, the refractive index n9 of the fluid f9 is modified to meet the expression (1). For example, variable amounts of sodium chloride may be dissolved in water to modify the specific gravity and concentration and thus the refractive index n9 of the fluid f9.

One candidate solute in this case is dipotassium hydrogen phosphate (K2HPO4). Dipotassium hydrogen phosphate has a high solubility and can significantly modify the specific gravity and concentration of the fluid f9 (i.e., the specific gravity and concentration can be varied over wide range). Thus, dipotassium hydrogen phosphate preferably has an advantage of ready modification of the refractive index n9 of the fluid f9 to an appropriate value.

When the equivalent phantom F is formed for imaging an interface between a cartilage and a meniscus of a knee joint, for example, in an exemplary configuration 3 that will be described later (see FIGS. 5A to 5C), the meniscus has greater specific gravity than the cartilage of the knee joint. Dissolution of significant amounts of dipotassium hydrogen phosphate in water as described above causes an increase in the specific gravity of the fluid f9 to exceed that of a columnar member f10 (corresponding to a cartilage of a knee joint), and the columnar member f10 and the fluid f9 can reproduce the ratio of the refractive index of the cartilage to that of the meniscus of the knee joint. Dipotassium hydrogen phosphate thus can readily and appropriately adjust the refractive index n9 of the fluid f9.

The liquid may be a solvent, such as alcohol and oil, other than water, and the solvent and a solute may be selected from appropriate materials.

Condition 2

The shape of the cylindrical member f8, which is composed of one of the first and second substances, should be at least partly identical the shape of the corresponding portion of a soft tissue.

If the cylindrical member f8 has a shape with a large radius substantially different from a cartilage of a phalangeal joint having a curvature radius of approximately 1 cm, or is not cylindrical but rectangular such an equivalent phantom F cannot be used to reproduce the profile of the pixel values I shown in FIG. 4 described later, even if the ratio n8/n9 of the refractive indices of the cylindrical member f8 to the fluid f9 corresponding to a soft tissue and the surrounding tissue is identical to the ratio nc/nt of the actual soft tissue to the surrounding tissue as in condition 1 described above.

In such a case, the shape (e.g., a curvature radius) of the cylindrical member f8 (formed of one of the first and second substances of the equivalent phantom F) should be identical to the shape of the corresponding portion of an actual soft tissue. The shape of the soft tissue is not the shape imaged in a differential phase image shown in FIG. 8B (the shape is viewed from the X-ray source 11a (i.e., from the upper area of FIG. 1)), but the shape of the soft tissue of the phalangeal joints placed on the object stage 13 and viewed from the proximal side to the distal side of the imaging apparatus 1 in FIG. 2 (i.e., the shape is viewed from the bottom to the top of FIG. 2, where the first, second, and third fingers are seen overlapped).

For example, the cylindrical member f8 should be formed such that the shape (e.g., curvature radius) of part of a cartilage of a phalangeal joint that can be represented by a circular arc in the top view is identical to the shape (e.g., the curvature radius) of the circle of the cylindrical member f8 of the equivalent phantom F in a front view shown in FIG. 3A.

A differential phase image generated through imaging of such an equivalent phantom F can reproduce the profile of the pixel values I (see FIG. 4) obtained from a differential phase image generated through imaging of an actual soft tissue.

Condition 3

The dose of X-rays passing through the housing f1 of the equivalent phantom F containing the first substance and the second substance is equal to the dose of X-rays passing through an object containing soft tissues corresponding to the equivalent phantom F.

As the thickness of the equivalent phantom F increases in the direction of incident X-rays (see D in FIG. 3A), the dose of the X-rays passing through the phantom decreases. A Moire image captured at a low dose of X-rays contains a high level of noise component, and the differential phase image (see ΔI in FIG. 4) from the Moire image also has a high level of noise component, which results in a differential phase image with a low S/N ratio.

In the evaluation of the quality of the X-ray Talbot imaging apparatus 1 from quality of a differential phase image generated from a Moire image obtained through imaging of the equivalent phantom F, the S/N ratio of the differential phase image may be different from the S/N ratio of a differential phase image of an actual object, which precludes appropriate evaluation of the image quality of the differential phase image. This phenomenon occurs if the dose of X-rays passing through the equivalent phantom F is different from the dose of X-rays passing through an object of a human body (e.g., the base of a finger) corresponding to the equivalent phantom F.

Preferably, the thickness D of the equivalent phantom F is adjusted to equalize the dose of X-rays passing through the housing f1 (of the equivalent phantom F) containing the first and second substances (the cylindrical member f8 and the fluid f9) irradiated with the X-rays from above as shown in FIGS. 3A and 3B to the dose of X-rays passing through an object (e.g., the base of a finger in the example above) containing a soft tissue corresponding to the equivalent phantom F.

If only the distance from the bottom f7 to the top lid f2 of the housing f1 is varied to adjust the thickness D of the equivalent phantom F without varying the amount of the fluid f9 in the housing f1 (i.e., only the top lid f2 is raised or lowered with air flowing into the housing f1), no change occurs on the dose of X-rays passing through the equivalent phantom F. The amount of the fluid f9 contained in the housing f1 thus varies together with a change in the thickness D of the equivalent phantom F, to vary the dose of X-rays passing through the equivalent phantom F.

According to the configuration described above, the S/N ratio in a differential phase image including the equivalent phantom F is equal to the S/N ratio in a differential phase image including an object of a human body corresponding to the equivalent phantom F. The S/N ratio in the differential phase image including the object of the human body corresponding to the equivalent phantom F can therefore be estimated from the S/N ratio in the differential phase image from the equivalent phantom F. The quality of the X-ray Talbot imaging apparatus 1 can also be appropriately determined from the image quality of the differential phase image including the equivalent phantom F.

Preferably, the equivalent phantom F should be formed for individual soft tissues as described above for the following reason. The imaging conditions of soft tissues (e.g., a cartilage and a tendon at a phalangeal joint and a knee joint), such as the ratio of the refractive index of the soft tissue to that of the surrounding tissue (condition 1), the shape (condition 2), the dose of X-rays passing through these tissues (condition 3), are different from each other. This phenomenon is applicable to exemplary configurations 2 to 4 described below.

The equivalent phantom F may further include another substance (not shown) in the housing f1 to reproduce not only a soft tissue and the surrounding tissue (e.g., a cartilage and joint fluid), but also, for example, a tissue supporting the soft tissue (e.g., a bone in a joint). For example, the equivalent phantom F may include three or more substances to reproduce a soft tissue, the surrounding tissue, and a tissue supporting the soft tissue (e.g., a cartilage, joint fluid, and a bone).

Exemplary Configuration 2

If a cartilage has some deformation, such as a defect with a length of several millimeters or even about several hundred micro-meters, due to arthritis and rheumatoid arthritis, the defect can be captured in a differential phase image at adequate visibility. To adjust the X-ray Talbot imaging apparatus 1 so as to capture such a fine structure in a differential phase image, the equivalent phantom F can be composed of the cylindrical member f8 having a small diameter of several hundred micro-meters as shown in FIGS. 3A to 3C according to the size of the deformation, such as the defect, in the cartilage.

If the cylindrical member f8 of the equivalent phantom F has a size as small as the size of the deformation of a soft tissue of a joint cartilage and if the quality of the X-ray Talbot imaging apparatus 1 is adjusted to appropriately capture the cylindrical member f8 of the equivalent phantom F in a differential phase image, the X-ray Talbot imaging apparatus 1 can capture not only a soft tissue but also a small deformation, such as a defect, in the soft tissue in the differential phase image.

The study of the inventors indicates that the X-ray Talbot imaging apparatus 1 can capture a differential phase image of a joint cartilage including defects of about 0.5 mm, although the resolution depends on the performance of the X-ray source 11a, the gratings 14 and 15, and the X-ray detector 16 (see FIG. 1). Thus, the X-ray Talbot imaging apparatus 1 can be adjusted with the equivalent phantom F including the cylindrical member f8 having a small diameter of about 0.5 mm to capture a differential phase image of a joint cartilage including deformation of about 0.5 mm.

If a part of the cylindrical member f8 of the equivalent phantom F has a shape equal to the shape of the corresponding portion of a soft tissue as described in condition 2 of the exemplary configuration 1, the curvature radius, for example, of the cylindrical member f8 of the equivalent phantom F should be equal to that of the corresponding portion of a soft tissue. In this case, the size, i.e., the diameter of the cylindrical member f8, is several centimeters, for example, about six centimeters at most.

Exemplary Configuration 3

If a cartilage has a large curvature radius, like a knee joint cartilage, the cylindrical member f8 also has a significantly large diameter to reproduce the curvature radius, resulting in a large thickness D of the housing f1 of the equivalent phantom F. Such equivalent phantom F cannot reproduce the dose of X-rays passing through an object.

Figure 5A:
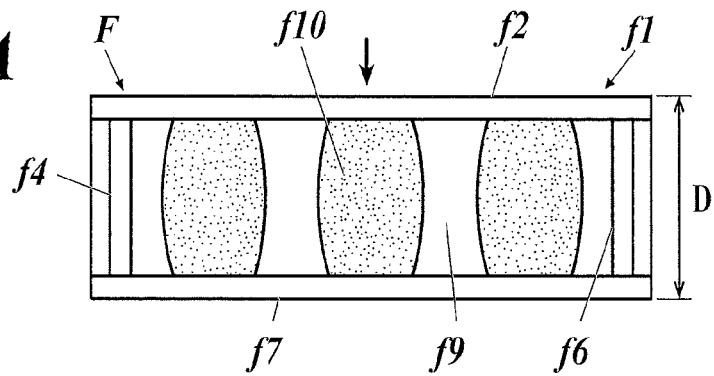
FIG. 5A is a front view illustrating another exemplary configuration of the equivalent phantom.
Figure 5B:
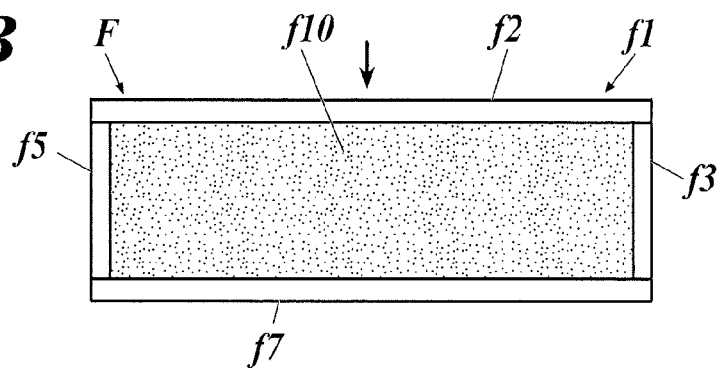
FIG. 5B is a side view illustrating the other exemplary configuration of the equivalent phantom.
Figure 5C:
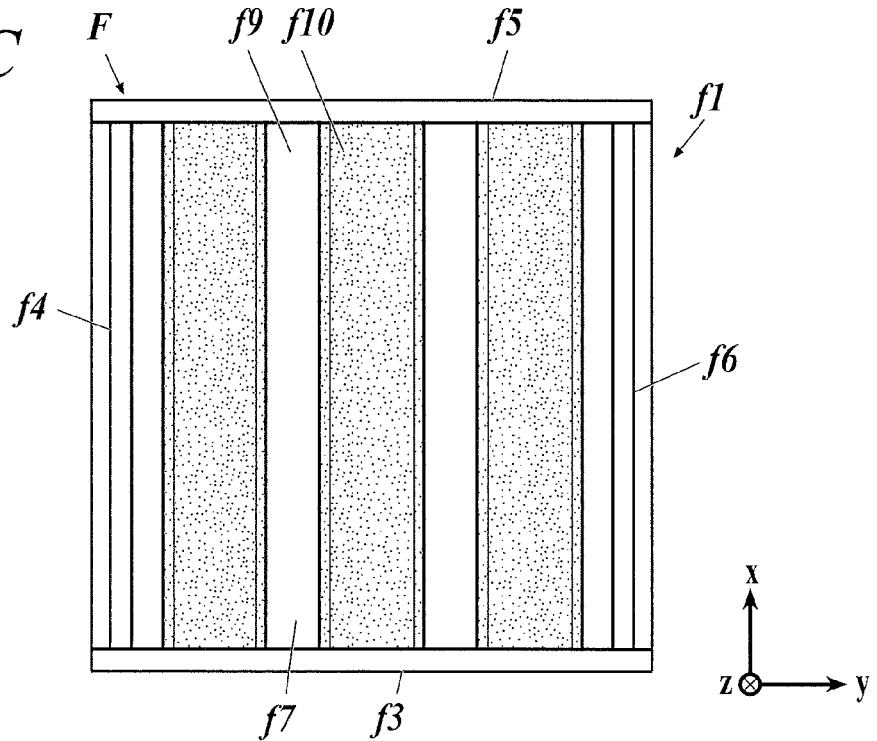
FIG. 5C is a plane view illustrating the other exemplary configuration of the equivalent phantom.

In that case, the equivalent phantom F may include the columnar member f10, instead of the cylindrical member f8, as shown in FIGS. 5A to 5C. The columnar member f10 has a cylindrical surface with a curvature radius identical to that of a soft tissue.

For example, the curvature radius of the cylindrical surface of the columnar member f10 is 20 to 100 mm for the equivalent phantom F corresponding to a relatively small joint such as an elbow joint, or 30 to 150 mm for the equivalent phantom F corresponding to a relatively large joint, such as a knee joint.

Exemplary Configuration 4

In the exemplary configurations 1 to 3, the first substance corresponding to a soft tissue among the first and second substances configuring the equivalent phantom F is the cylindrical member f8 or the columnar member f10. Alternatively, the first substance corresponding to the soft tissue may be a spherical member f11, for example, as shown in FIGS. 6A to 6C.

The equivalent phantom F configured as in the exemplary configurations 3 and 4 also have the same functions and advantage as that of the exemplary configurations 1 and 2.

Figure 6A:
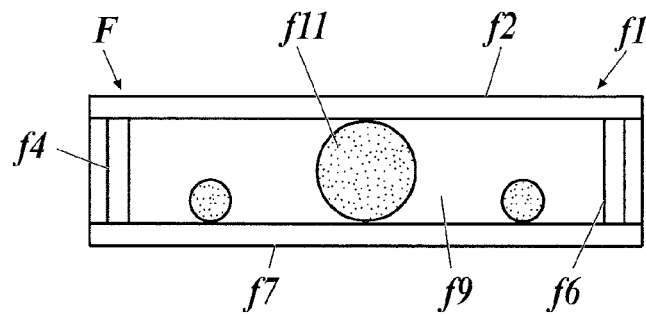
FIG. 6A is a front view illustrating another exemplary configuration of the equivalent phantom.
Figure 6B:
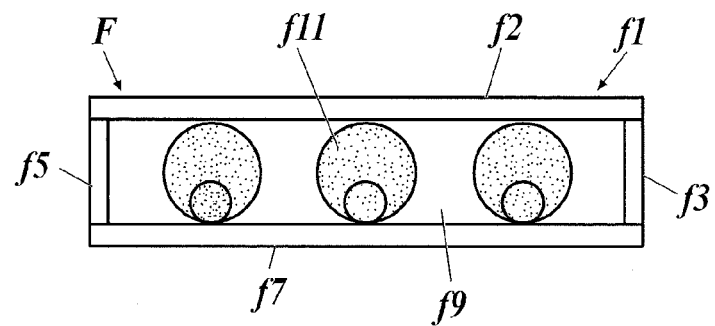
FIG. 6B is a side view illustrating the other exemplary configuration of the equivalent phantom.
Figure 6C:
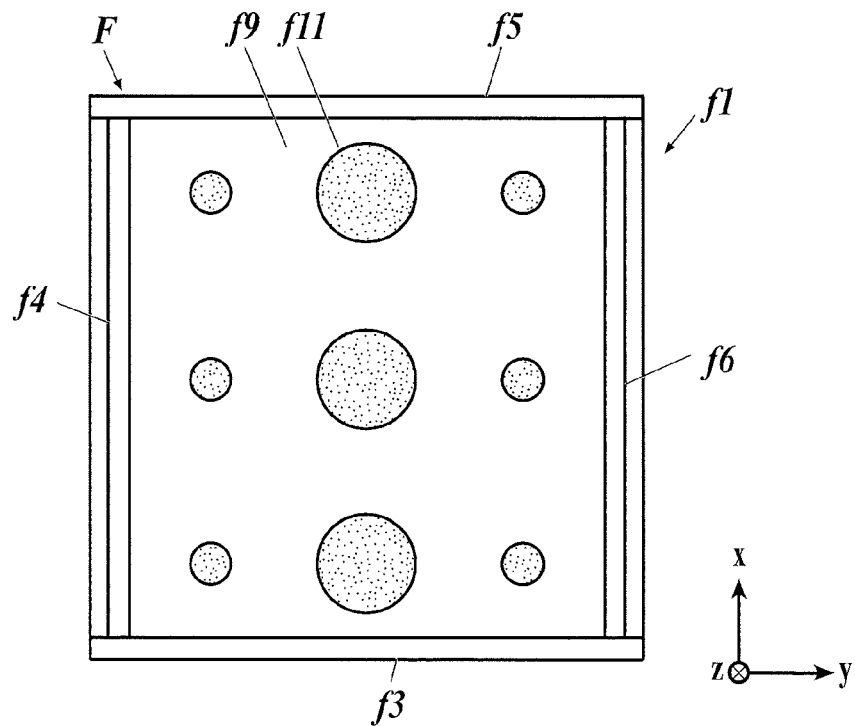
FIG. 6C is a plane view illustrating the other exemplary configuration of the equivalent phantom.

In the exemplary configuration 4, the housing f1 of the equivalent phantom F may contain spherical members f11 having different sizes (radii), for example, as shown in FIGS. 6A to 6C. In the exemplary configurations 1 to 3, the housing f1 (not shown) of the equivalent phantom F may contain the cylindrical member(s) f8 and the columnar member(s) f10 having different sizes (radii and curvature radii).

The housing f1 of the equivalent phantom F may contain the cylindrical member f8, the columnar member f10, and the spherical member f11. This indicates that the equivalent phantom F may be formed by any appropriate combination of the exemplary configurations 1 to 4.

Each exemplary configuration described above includes the cylindrical member f8 (exemplary configurations 1, 2), the columnar member f10 having the cylindrical surface (exemplary configuration 3), and the spherical member f11 (exemplary configuration 4), as substances corresponding to soft tissues. This configuration is based on the condition that a cartilage at a joint generally has a portion that can be represented by a circular arc. If the soft tissue is a tumor mass or the like, any shape other than a circular arc may represent the shape of the soft tissue. Thus, the substance corresponding to a soft tissue may have any shape other than a columnar member having a cylindrical member or a cylindrical surface, and a spherical member. For example, the substance may have any appropriate shape mimicking a defect of a cartilage.

Evaluation of Quality of X-Ray Talbot Imaging Apparatus with Equivalent Phantom

A method of evaluating the quality of the X-ray Talbot imaging apparatus 1 with the equivalent phantom F will now be described.

The equivalent phantom F of the embodiment is irradiated with X-rays to capture a Moire image. The Moire image is reconstructed to a differential phase image (or, an image generated from a differential phase image, hereinafter). The generated differential phase image has a profile of a pixel values I at an interface between the first substance (e.g., the cylindrical member f8) of the equivalent phantom F corresponding to a soft tissue and the other substance (the fluid f9) as show in FIG. 4.

As described above, in the equivalent phantom F of the embodiment, the ratio between the two refractive indices (e.g., of the cylindrical member f8 and the fluid f9) is equal to that between a soft tissue (e.g., a cartilage) and the surrounding tissue (e.g., joint fluid and meniscus) and the shape of one of the two substance corresponding to a soft tissue (e.g., the cylindrical member f8) is at least partly equal to that of the soft tissue. The profile of a pixel values I in this case is equal to or very similar to that at the interface between a cartilage and joint fluid in a differential phase image from an actual human joint shown in FIG. 8B, for example.

The profile of the pixel values I (shown in FIG. 4) obtained through capturing the equivalent phantom F, therefore, can be used to evaluate the image quality of a differential phase image, and then the image quality can be used to evaluate the quality of the X-ray Talbot imaging apparatus 1.

Specifically, if the signal on the pixel value clearly appears at a portion corresponding to the interface between a cartilage and joint fluid in the differential phase image (see the arrow shown in FIG. 8B), the differential phase image have high visibility. The signal indicating the maximum pixel value I is represented by the Imax in FIG. 4.

In FIG. 4, as the difference increases between the maximum value Imax and the mean value Iave (or the minimum value Imin) of the pixel values I, the signal indicating the interface between the soft tissue and the surrounding tissue in the differential phase image increases, resulting in high image quality. This difference between the maximum value Imax and the mean value Iave (or the minimum value Imin) of the pixel values I in FIG. 4 may be used as an index for evaluation of the image quality of the differential phase image, i.e., the quality of the X-ray Talbot imaging apparatus 1.

Even if the differential phase image has a large maximum value Imax (Imax−Iave, or Imax−Imin) at the interface in the image between a soft tissue and the surrounding tissue but has a low S/N ratio at the interface, the maximum value is indistinctive due to a high noise level $\Delta I$. Therefore, (Imax−Iave)/$\Delta I$ (see FIG. 4), which is the $\Delta I$ and the S/N ratio showing a noise level in the pixel values I in the profile, may be used as an index for evaluation of the image quality of the differential phase image, i.e., the quality of the X-ray Talbot imaging apparatus 1. In FIG. 4, the noise $\Delta I$ is defined as a difference between the maximum value and the minimum value of the pixel values I in a limited area. Alternatively, a standard deviation Istd in a limited area in the profile or a standard deviation Istd' in a limited area in the image may be used for the $\Delta I$.

In this case, the X-ray Talbot imaging apparatus 1 may be evaluated from a magnitude of the S/N ratio (Imax−Iave)/$\Delta I$ (or (Imax−Iave)/Istd, hereinafter) and a noise $\Delta I$ in the image area of the differential phase image where X-rays pass through one of the first and second substances in the equivalent phantom F (e.g., pass through the cylindrical member f8 and the columnar member f10). Also, the S/N ratio and the noise $\Delta I$ at an area in an image corresponding to the first and second substances of the equivalent phantom F may be used to evaluate the X-ray Talbot imaging apparatus 1.

The maximum value Imax (e.g., Imax−Iave), the noise $\Delta I$, and the S/N ratio of the pixel values I at an interface may be listed in a control table, for example, shown in FIG. 7. The "Cylindrical member" of the equivalent phantom F indicates the shape of the exemplary configuration 1.

The quality of the X-ray Talbot imaging apparatus 1 may be evaluated by comparison of the latest evaluated results with previous evaluated results in the control table (see FIG. 7). The same equivalent phantom F as that used in the latest evaluation is irradiated with X-rays under the same conditions to capture a Moire image. The Moire image is used to generate a differential phase image and a profile of pixel values I at an interface as shown in FIG. 4. The maximum value Imax, the noise $\Delta I$, and the S/N ratio (Imax−Iave)/$\Delta I$ of the pixel values I at the interface are calculated. These calculated values (i.e., the latest evaluated results) are compared with the previous evaluated results in the control table to check for quality degradation of the X-ray Talbot imaging apparatus 1.

If the quality of the X-ray Talbot imaging apparatus 1 is regarded as deteriorated, any necessary actions will be taken, such as replacement of the X-ray source 11a, the gratings 12, 14, 15, and/or the X-ray detector 16 (see FIG. 1).

In addition to the control, maintenance, or improvement of the quality of the X-ray Talbot imaging apparatus 1, an equivalent phantom F including a cylindrical member f8 having a small diameter as shown in the exemplary configuration 2 can be used for an enhancement of the performance of the X-ray Talbot imaging apparatus 1 to capture a small deformation, for example, of defect in a cartilage.

As described above, the equivalent phantom F of the embodiment can be used for control, maintenance, or improvement of the quality, and/or enhancement of the performance, of the X-ray Talbot imaging apparatus 1.

Advantageous Effect

According to the embodiments, the equivalent phantom F includes the first and second substances (i.e., a combination of the cylindrical member f8, columnar member f10, or the spherical member f11 with the fluid f9); the ratio between the refractive indices of the first and second substances is equal to that between a soft tissue such as a cartilage and the surrounding tissue (e.g., joint fluid, meniscus) at a joint; and, the shape of the substance for the soft tissue (i.e., the substance for the cylindrical member f8, the columnar member f10, or the spherical member f11) is equal at least partly to the corresponding portion of the soft tissue.

Such equivalent phantom F can properly reproduce the shape of the soft tissue with the substances (the substance for cylindrical member f8, the columnar member f10, or the spherical member f11), as well as the ratio of the refractive index of the soft tissue to that of the surrounding tissue with the first substance, i.e., the cylindrical member f8, columnar member f10, and spherical member f11, and the second substance, i.e., the fluid f9.

The equivalent phantom F is irradiated with X-rays to capture a Moire image, from which a differential phase image is generated. The differential phase image has an area of the first and second substances of the equivalent phantom F. The area can reproduce a profile (see FIG. 4) of pixel values I in a differential phase image of an actual soft tissue and the surrounding tissue.

In conclusion, the equivalent phantom F according to the embodiment can be used for control, maintenance, and improvement of the quality of, and for enhancement of performance of the X-ray Talbot imaging apparatus 1.

It should be understood that the exemplary configurations described above should not be construed to limit the present invention and any variation of the exemplary configurations may be made without departing from the scope of the invention.

This U.S. patent application claims priority to Japanese patent application No. 2014-099195 filed on May 13, 2014, the entire contents of which are incorporated by reference herein for correction of incorrect translation.

What is claimed is:

1. An equivalent phantom for an X-ray Talbot imaging apparatus which comprises an X-ray source, a plurality of gratings and an X-ray detector, and which captures at least a Moire image from which a differential phase image of an object is generated, the equivalent phantom comprising:
    a first substance having a first refractive index; and
    a second substance having a second refractive index,
    wherein a ratio of the first refractive index to the second refractive index is equal to a ratio of a refractive index of a soft tissue to a refractive index of a surrounding tissue, and
    wherein at least a part of a shape of one of the first and second substances is equal to a shape of a corresponding portion of the soft tissue.

2. An equivalent phantom according to claim 1, wherein the at least part of the shape of the one of the first and second substances is defined by a radius, a diameter, or a curvature radius.

3. An equivalent phantom according to claim 1, wherein a size of the one of the first and second substances is equal to a size of the soft tissue or a size of a deformation of the soft tissue.

4. An equivalent phantom according to claim 1, wherein the first and second substances are accommodated in a housing.

5. An equivalent phantom according to claim 4, wherein a dose of X-rays passing through the housing accommodating at least the first and second substances is equal to a dose of X-rays passing through the object including the soft tissue when an image of the object is captured.

6. An equivalent phantom according to claim 1, wherein the second substance comprises liquid, and
    wherein the specific gravity or concentration of the liquid is adjusted such that the ratio of the first refractive index to the second refractive index is identical to the ratio of the refractive index of a soft tissue to the refractive index of the surrounding tissue.

7. A method of evaluating quality of an X-ray Talbot imaging apparatus comprising:
    an X-ray source which emits X-rays;
    a plurality of gratings; and
    an X-ray detector which includes conversion elements which generate electric signals in accordance with the emitted X-rays, and which reads the electric signals generated at the conversion elements as a Moire image,
    the method comprising:
    emitting X-rays from the X-ray source to the equivalent phantom of claim 1 to capture the Moire image;
    generating, from the Moire image of the equivalent phantom, at least a differential phase image or an image based on the differential phase image; and
    evaluating the quality of the X-ray Talbot imaging apparatus with the generated differential phase image or the image based on the differential phase image.

8. A method of evaluating the quality of the X-ray Talbot imaging apparatus with the equivalent phantom according to claim 7, wherein the quality of the X-ray Talbot imaging apparatus is evaluated based on the maximum pixel value at an interface between a first substance and a second substance of the equivalent phantom in the generated differential phase image or the image based on the differential phase image.

9. A method of evaluating the quality of the X-ray Talbot imaging apparatus with the equivalent phantom according to claim 7, wherein the quality of the X-ray Talbot imaging apparatus is evaluated based on a noise level or a S/N ratio in an image area where X-rays pass through at least one of the substances of the equivalent phantom in the generated differential phase image or the image based on the differential phase image.

* * * * *